United States Patent [19]

Tremulis

[11] Patent Number: 5,242,394
[45] Date of Patent: Sep. 7, 1993

[54] STEERABLE DILATATION CATHETER

[75] Inventor: William S. Tremulis, Redwood City, Calif.

[73] Assignee: Advanced Cardiovascular Systems, Inc., Santa Clara, Calif.

[21] Appl. No.: 882,481

[22] Filed: May 13, 1992

Related U.S. Application Data

[63] Continuation of Ser. No. 231,215, Aug. 11, 1988, which is a continuation-in-part of Ser. No. 760,636, Jul. 30, 1985, abandoned.

[51] Int. Cl.⁵ ............................................. A61M 37/00
[52] U.S. Cl. ........................................ 604/95; 604/96; 604/170; 128/657; 128/772
[58] Field of Search ................... 604/95, 96, 102, 164, 604/170, 280, 281, 282; 128/656, 657, 658, 772

[56] References Cited

U.S. PATENT DOCUMENTS

| | | |
|---|---|---|
| 3,890,977 | 6/1975 | Wilson . |
| 4,037,324 | 7/1977 | Andreasen . |
| 4,411,655 | 10/1983 | Schreck . |
| 4,425,908 | 1/1984 | Simon . |
| 4,427,000 | 1/1984 | Ueda . |
| 4,503,569 | 3/1985 | Dotter . |
| 4,505,767 | 3/1985 | Quin . |
| 4,512,338 | 4/1985 | Balko et al. . |
| 4,665,906 | 5/1987 | Jervis . |
| 4,867,173 | 9/1989 | Leoni ............................. 604/170 X |
| 4,884,579 | 12/1989 | Engelson ....................... 604/170 X |
| 4,925,445 | 5/1990 | Sakamoto et al. . |
| 4,934,340 | 6/1990 | Ebling et al. . |
| 4,934,380 | 6/1990 | de Toledo ........................ 604/95 X |
| 4,984,581 | 1/1991 | Stice . |
| 5,025,799 | 6/1991 | Wilson . |
| 5,120,308 | 6/1992 | Hess .................................... 604/95 |

*Primary Examiner*—John D. Yasko
*Attorney, Agent, or Firm*—Crosby, Heafey, Roach & May

[57] ABSTRACT

A low-profile steerable dilatation catheter for angioplasty procedures which has an inflated balloon on the distal end with little or no tendency to wrap on itself when the catheter is advanced through a patient's vascular system. The catheter comprises an elongated tubular member which is longitudinally relatively flexible but diametrically relatively rigid, a guide extension secured to the distal end of the elongated tubular member, and an inflatable balloon secured on the proximal end thereof to the distal end of the elongated tubular member and on the distal end directly or indirectly to the guide member or the tubular member and an elongated flexible member such as a helical coil secured to the guide extension distally of the balloon. The elongated tubular member is preferably a hypotube of stainless steel or nitinol.

6 Claims, 3 Drawing Sheets

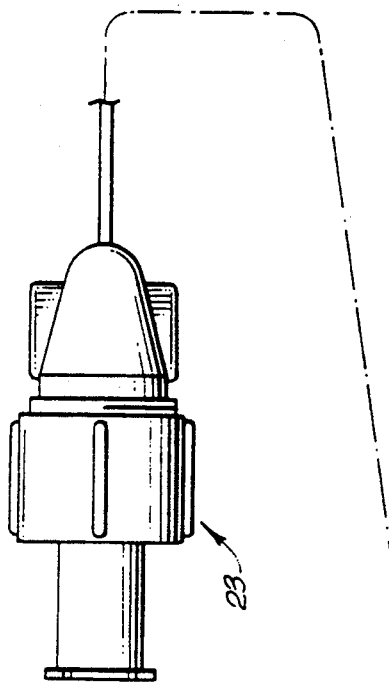
Fig. 1
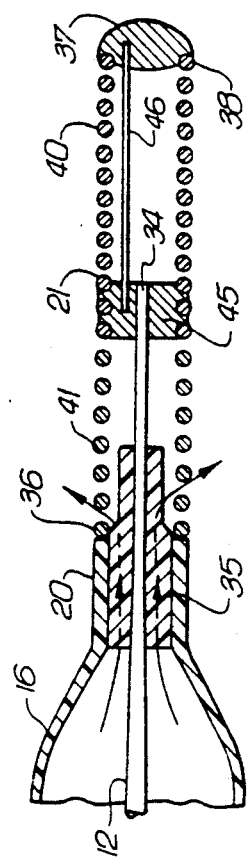
Fig. 2
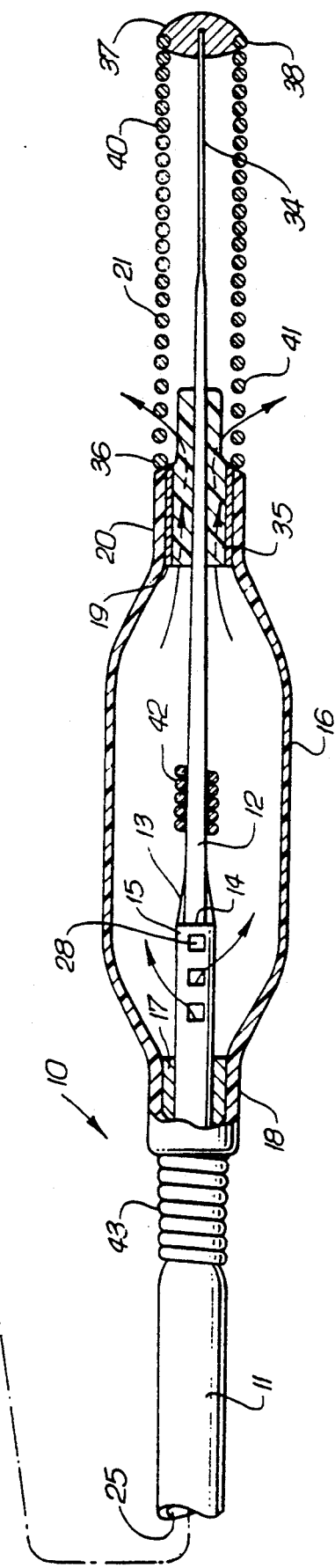

STEERABLE DILATATION CATHETER

This is a continuation of the application Ser. No. 07/231,215, which was filed on Aug. 11, 1988, pending which is a continuation-in-part of Ser. No. 06/760,636 filed Jul. 30, 1985 now abandoned.

BACKGROUND OF THE INVENTION

This invention generally relates to vascular catheters and particularly low-profile steerable catheters for angioplasty procedures, such as percutaneous transluminal coronary angioplasty (PTCA).

In PTCA procedures, a dilatation catheter having an inflated balloon on the distal end thereof is advanced through a patient's arterial system until the deflated balloon crosses the atherosclerotic lesion to be dilated. The balloon is inflated to a predetermined size with radiopaque liquid at relatively high pressures to compress the atherosclerotic plaque against the inside of the artery wall and then the balloon is deflated so that the catheter can be removed and blood flow resumed.

Typically, a guiding catheter having a preformed distal end is first percutaneously introduced into the patient's arterial system with the distal tip in the coronary artery. A guidewire is advanced through the guiding catheter into the patient's coronary anatomy until the distal end of the guidewire crosses the lesion to be dilated. The dilatation catheter is then advanced over the guidewire, with the guidewire slidably disposed within an inner lumen of the catheter, until the inflatable balloon is positioned within the lesion. For a more detailed description of angioplasty procedures and the devices used in such procedures, reference is made to U.S. Pat. No. 4,332,254 (Lundquist); U.S. Pat. No. 4,323,071 (Simpson-Robert); U.S. Pat. No. 4,439,185 (Lundquist); U.S. Pat. No. 4,468,224 (Enzmann et al.) U.S. Pat. No. 4,516,972 (Samson); U.S. Pat. No. 4,538,622 (Samson et al.); and U.S. Pat. No. 4,616,652 (Simpson) which are hereby incorporated herein in their entirety.

Steerable dilatation catheters with built-in guidewires or guiding elements are being used with greater frequency because the deflated profile of such catheters are generally smaller than conventional dilatation catheters having the same inflated balloon size. Further details of low-profile steerable dilatation catheters may be found in U.S. Pat. No. 4,582,181 (Samson) which is hereby incorporated in its entirety by reference thereto. The lower profile of these catheters allows the catheter to cross tighter lesions and to be advanced much deeper into the patient's coronary anatomy. Moreover, the use of steerable low-profile dilatation catheters having a built-in guidewire or guiding element shortens considerably the time for the angioplasty procedures because there is no need to first insert a guidewire and then insert a conventional dilatation catheter over the previously inserted guidewire.

However, it has been found that the balloon elements of commercially available very low-profile steerable catheters tend to wrap on themselves when the catheter is torqued so that the balloon frequently will not completely inflate when positioned across a stenosis or if inflated to deflate within a desired time period. Some suppliers of such catheters recommend that the catheter be limited to one rotation to avoid such balloon wrapping. However, such restrictions on rotations severely limit the steerability of the catheter within a patient's vasculature.

What has been needed and heretofore unavailable is a steerable dilatation catheter having a very low profile which can be torqued from the proximal end thereof without wrapping the inflatable balloon element. The present invention satisfies this and other needs.

SUMMARY OF THE INVENTION

This invention is directed to a steerable dilatation catheter having an inflatable balloon which has a very low profile and which will not wrap on itself upon torqueing.

The steerable dilatation catheter in accordance with the present invention includes an elongated tubular member having proximal and distal portions, an inner lumen extending along the length thereof, and one or more inflation ports in the distal portion in fluid communication with the inner lumen thereof. The tubular member is relatively flexible in the longitudinal direction, but diametrically it is relatively rigid. A guide extension or element, which is preferably tapered toward its distal end, is secured by suitable means at its proximal end to the distal end of the elongated tubular member. An inflatable balloon is concentrically disposed at least in part about the tubular member with the proximal end of the balloon secured by suitable means to the tubular member proximal to one or more of the inflation ports therein being in fluid communication with the interior of the inflatable balloon to facilitate the inflation thereof. The distal end of the balloon is sealingly secured about the distal extremity of the tubular member or the guide extension so that little or no relative rotational movement occurs between the ends of the balloon during the torquing of the catheter when it is steered through the patient's arterial system. An elongated flexible member such as a helical coil or a cylindrical plastic member (e.g., polyethylene) having a rounded plug on the distal end is coaxially disposed about the guide extension and extends distally of the balloon. It is joined by suitable means to the guide extension at one or more locations along the length thereof.

The structure of the catheter tip distally of the balloon can be of standard design wherein the distal tip of the guide extension is secured to the rounded plug at the distal tip of the coil. Alternatively, it may have a floppy design wherein the distal tip of the coil extends beyond the distal tip of the guide extension and a safety ribbon extends from an intermediate location to the rounded plug in the distal tip of the coil where it is secured.

The proximal end of the elongated tubular member has an adapter with means to introduce inflating liquid into the inner lumen of the tubular member and also means to apply torque to the tubular member in order to provide steerability to the dilatation catheter.

The low-profile steerable dilatation catheter of the invention can be used by itself to dilate tight stenoses, or it can be used in conjunction with a larger diameter conventional dilatation catheter as described in copending application Ser. No. 760,636 filed Jul. 30, 1985, which is hereby incorporated in its entirety herein. As described in the above copending application, when it is found during an angioplasty procedure that the deflated balloon of a conventional dilatation catheter is too large to cross a stenotic region to be dilated, the steerable low-profile catheter of the invention is advanced through an inner lumen of the conventional dilatation catheter until the balloon of the low-profile catheter is in the stenotic region. The balloon is inflated to dilate the stenosis sufficiently so that the conventional dilatation balloon can be advanced over the low-profile dilatation cathter in place to position the balloon of the conventioal catheter across the stenosis so that upon inflation thereof the dilation can be complete.

In a presently preferred embodiment, the elongated tubular member is a hypotube formed of stainless steel (e.g., type 304) or other suitable materials, such as nitinol, which is a nickel-titanium alloy having a "memory" and superelastic properties. The use of hypotubes in such instances allows the dilatation catheter to be made with profiles as low as 0.010 inch (0.254 mm). Moreover, even though the hypotube is formed of high-strength materials and is diametrically rather rigid, the diameter-to-length ratio is sufficiently low that the elongated tubular member made therefrom is relatively flexible. It can be easily advanced through the tortuous arterial passages of a patient and it has excellent pushability.

In one presently preferred embodiment, the distal end of the tubular member terminates within the interior of the balloon. In this instance, the guide element, which is secured to the distal end of the tubular member, extends through the distal end of the balloon. In another presently preferred embodiment, the tubular member extends through the interior of the balloon. However, in this embodiment, a plurality of slots are formed in the wall of the tubular member extending through the balloon to increase the flexibility without significantly reducing the torquability thereof.

In accordance with the invention, both ends of the inflatable balloon are fixed so there is little or no tendency for the balloon to wrap on itself when the catheter is torqued from the proximal end during the advancement of the catheter through the patient's arteries.

These and other advantages of the dilatation catheter of the invention will become more apparent from the following detailed discussion thereof when taken in conjunction with the accompanying exemplary drawings.

BRIEF DESCRIPTION OF THE DRAWINGS

FIG. 1 is an elevational view, partially in section, of a steerable dilatation catheter embodying features of the invention;

FIG. 2 is a sectional view of the distal portion of an alternate embodiment having a floppy tip.

DETAILED DESCRIPTION OF THE INVENTION

Figure 3:
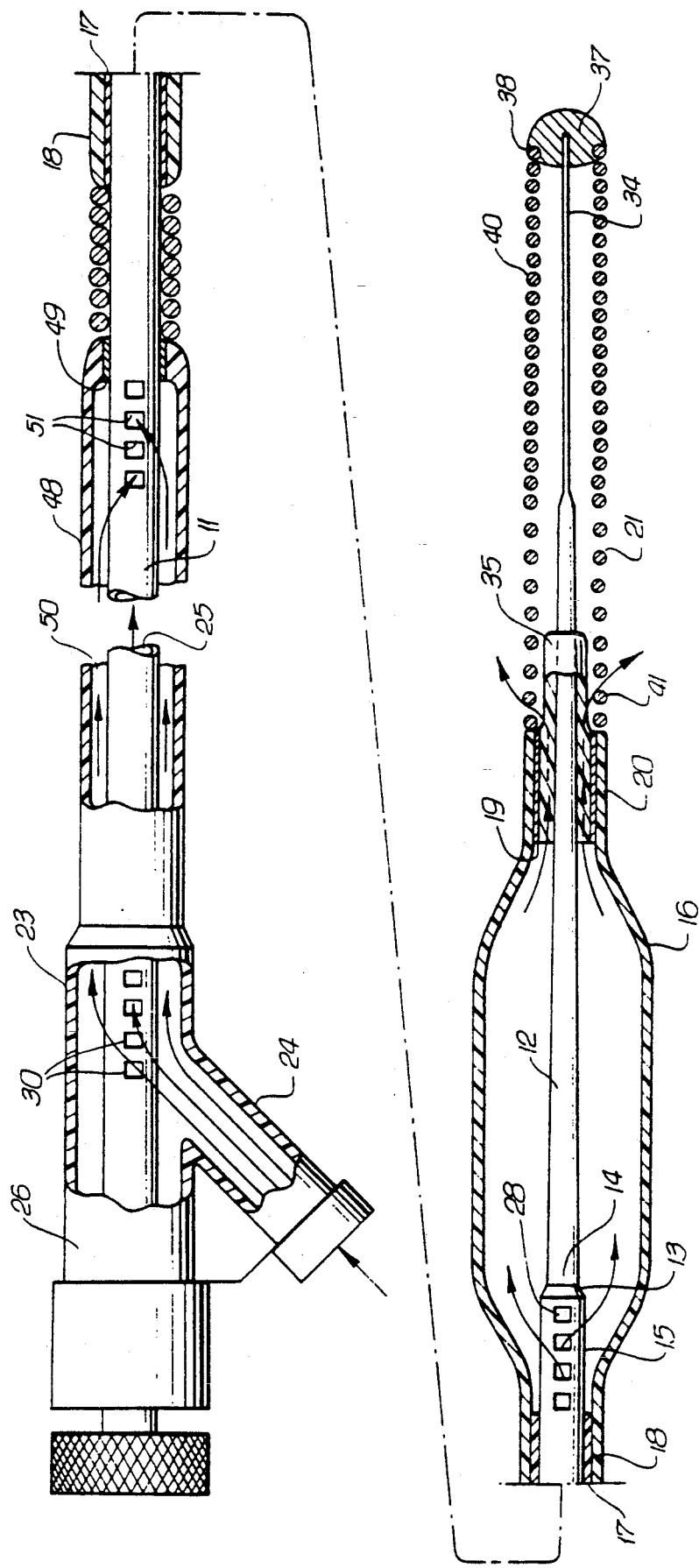
FIG. 3 is an elevational view, partially in section, of another alternative steerable dilatation catheter embodying features of the invention.

FIG. 1 illustrates a steerable dilatation catheter assembly 10 embodying features of the invention. As shown, the catheter assembly 10 generally comprises an elongated tubular member 11, a guide extension 12 joined by soldering or brazing 13 at the proximal end 14 thereof to the distal end 15 of the tubular member 11, a balloon element 16 secured by suitable adhesive 17 at the proximal end 18 thereof to distal end 15 of the tubular member 11 and by adhesive 19 at the distal end 20 to the guide extension 12, and a flexible coil 21 secured to the guide extension 12 at a suitable location distally of the balloon 16. A removable hub 23 such, as the luer lock shown, is connected to the proximal end of the elongted tubular member 11 to facilitate connection to a source for radiopaque inflation fluid. The hub 23 when tightened against tubular member 11 permits torquing of the proximal end of the tubular member 11 which extends therethrough to steer the catheter when it is advanced through a patient's vasculature.

The elongated tubular member 11 is preferably a hypotube formed from stainless steel, such as type 304 stainless steel, or other suitable materials such as nitinol, and has an inner lumen 25 extending along the length thereof. It has one or more ports 28 in the distal portion 15 thereof to discharge inflation fluid from the inner lumen 25 into the interior of the balloon element 16 for the inflation thereof. Inflation fluid is introduced into the inner lumen 25 through hub 23. Typical dimensions of the tubular member include a length of about 150 cm, an outside diameter of 0.018 inch (0.457 mm), and an inside diameter of 0.012 inch (0.305 mm) in the proximal portion which tapers to an outside diameter of 0.01 inch (0.254 mm) in the distal portion. The tubular member can be tapered in steps along its length. These steps can be formed by drawing the tubing or by joining sections of tubing having sequentially smaller diameters by brazing, soldering, welding and the like.

The proximal end 14 of the guide extension 12 is suitable secured to the distal end 15 of the tubular member 11 such as by soldering, brazing, or welding as shown at 13. Preferably, the proximal end 14 of the guide extension 12 is sized to fit within the distal end 15 of tubular member 11. The guide element 12 tapers in the distal direction to smaller diameters to provide greater flexibility to the distal end of the catheter assembly 10. The most distal portion 34 of guide extension 12 is preferably flattened to provide even greater flexibility in a single plane and also to facilitate its manual shaping. The guide element 12 may be made of stainless steel or other suitable materials, such as nitinol. Moreover, it can be in the form of a solid rod or a helical coil or wire or combination thereof. The length of the guide element may generally range from about 2 to about 6 cm depending upon tip design. The most distal flattened portion 34 of guide element 12 typically has a transverse cross section of 0.001 by 0.003 inch (0.025 by 0.076 mm).

The proximal end of inflatable balloon element 16 is secured by adhesive 17 to the distal extremity 15 of the tubular element 11 so that one or more of the discharge ports 28 are disposed within the interior of the balloon element 16. The distal end 20 of the balloon 16 is sealingly secured by adhesive 19 either directly to the guide extension 12 or indirectly through porous plastic element 35 to seal the interior of the balloon element 16 and prevent the escape of inflation liquid when the balloon is inflated. The balloon element 16 is preferably formed from flexible but relatively inelastic materials, such as irradiated polyethylene or polyethylene terephthalate. The proximal and distal ends 18 and 20, respectively, of the balloon 16 may also be heat shrunk onto the tubular member 11 and extension 12 if the balloon is made from heat shrinkable material. Preferably, a porous plastic sheath 35, formed of material such as porous polypropylene, is positioned between the distal end 20 of the balloon 16 and the guide element 12 to allow for the escape of air (as shown by the arrows) but not liquid when the balloon is filled with inflation liquid. Other suitable means for venting air when the balloon is filled with liquid include a small conduit, such as described in U.S. Pat. No. 4,638,805 (Powell). Alternatively, microscopic holes may be drilled in the balloon element as described in copending application Ser. No. 000,651, filed Jan. 6, 1987.

Flexible coil 21 is coaxially disposed about the guide extension 12 and is directly or indirectly secured thereto by at least the proximal end 36 thereof. Suitable joining means include brazing, soldering, or adhesives. A smooth round plug 37 of solder or brazement is provided at the distal tip 38 to reduce the trauma to the interior of the patient's vascular system when the catheter is advanced therein. Preferably, the entire coil section is formed of radiopaque metal, such as platinum, tungsten, irridium, rhenium, gold and alloys thereof to permit observation thereof under fluoroscopic examination. The plug 37 may be similarly formed of radiopaque materials. The distal coil section 40 is given a small stretch (e.g., 10%) to provide a greater degree of flexibility to the tip. If desired, the proximal coil section 41 may be formed from stainless steel (e.g., type 304) or other suitable materials. Radiopaque marker coils 42 and 43 may be also provided about the guide element 12 and about the tubular member 11, respectively, to aid in locating the proximal and central portions of the balloon 16 during fluoroscopic examination.

An alternate embodiment, commonly termed a floppy design, is shown in FIG. 2 wherein the distal end 34 of the guide element 12 does not extend to the distal end 38 of the coil 21 but instead is joined to the coil by brazing or soldering at an intermediate location 45. A safety or shaping ribbon 46 extends from the brazement at location 45 to the plug 37. The ribbon 46 can be manually bent or curved to facilitate the entry of the distal end of the catheter into a desired blood vessel during angioplasty procedures. In a presently preferred embodiment, the safety ribbon 46 is formed of material stronger than the material of the guide extension such as tungsten or tungsten alloys and has typical transverse cross-sectional dimensions of 0.001×0.003 inch (0.025×0.076 mm).

Another alternate embodiment is shown in FIG. 3 wherein a flexible plastic tubular element 48 is disposed concentrically about the tubular member 11 and wherein the plastic tubular element is sealingly secured about the periphery of the tubular member 11 at a location 49 by suitable means such as adhesive proximally of the balloon 16. This construction directs inflation fluid passing within the annular passageway 50 between the outer tubular member 48 and the inner tubular member 11 into the interior of the latter through inlet ports 51. The inflation fluid passes through the inner lumen 25 of the tubular member 11 and flows out of discharge ports 28 into the interior of the balloon element 16 as described in the previous embodiment.

Figure 4:
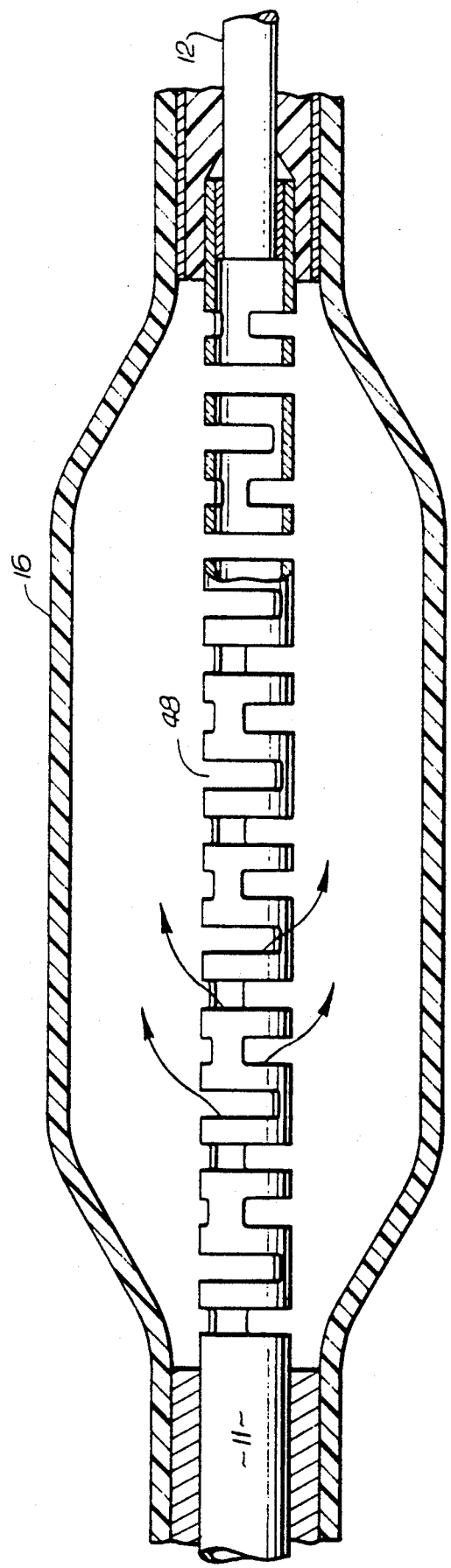

FIG. 4 represents an alternate embodiment of the invention wherein tubular member 11 extends through the interior of the balloon 16 and guiding element 12 is secured to the distal portion of the tubular member 11 which extends through the distal end of balloon 16. To provide additional flexibility to the portion of the tubular member 11 which extends through the balloon, a plurality of slots 48 are formed in the wall of the tubular member 11, preferably with each slot axially set off from the adjacent slot by at least 45°. The slots can be formed by any suitable means such as by cutting with blade or laser, etching, and the like. The width and depth of the slots, the distance between the slots, the angular disposition about the perimeter of the tubular member and the angular orientation with respect to the longitudinal axis can be adjusted to vary the flexibility and torquing characteristics of the tubular member. Preferably, the width of the slots ranges from about 0.01 to about 0.034 inch (0.254 to 1.02 mm) and the distance between slots ranges from about 0.02 to about 0.08 inch (0.508 to 0.203 mm). The slots should extend more than halfway through the diameter of the tubular member 11. A similar structure can be obtained by replacing the slotted tubular section with a helical coil.

Typical dimensions of the steerable, low-profile dilatation catheter of the invention include an overall length of approximately 150 to about 200 cm, a tip coil length from about 1 to 3 cm, a balloon length of about 1 to 3 cm, and inflated balloon diameters from about 1 to about 5 mm. Deflated profiles for the balloon range from about 0.01 to about 0.025 inch (0.254 mm–0.635 mm), preferably less than about 0.02 (0.508 mm) inch, so that the dilatation catheter can be inserted through an inner lumen of a standard dilatation catheter as disclosed in U.S. patent application Ser. No. 760,636, filed Jul. 30, 1985.

The low-profile steerable dilatation catheter of the invention can be used in the same manner as prior low-profile steerable dilatation catheters. However, because of the smaller profiles available with the dilatation catheters of the present invention, much tighter stenoses can be crossed than with prior devices. Moreover, the dilatation catheter of the invention can be readily advanced through very tortuous arterial passageways with little risk of wrapping the balloon on itself thus ensuring complete inflation and deflation when it is positioned within a stenosis to be dilated. Additionally, the dilatation catheter can be used as described in copending application Ser. No. 760,636 to be disposed within the inner lumen of a standard dilatation catheter in order to first dilate a stenosis so that the larger profile standard dilatation catheter can then be inserted therein to complete the dilatation. The luer lock connection on the proximal end of the tubular member in accordance with the invention provides the further advantage that the luer connection can be removed, an exchange wire inserted into the proximal end of the tubular member and a standard dilatation catheter can be advanced over the low-profile steerable catheter of the invention. Other uses of the invention will become apparent.

While the above description of the invention is directed to presently preferred embodiments, various modifications and improvements can be made without departing from the scope of the invention.

What is claimed is:

1. A steerable dilatation catheter comprising:
   a) an elongated torquable member which has
      a proximal tubular element having proximal and distal ends, having an inner lumen extending therein and being formed of a material selected from the group consisting of stainless steel and NiTi alloy;
      a distal core element having proximal and distal ends, being secured to the distal end of the proximal torquable member and being formed of NiTi alloy;
      a flexible coiled member disposed about and secured to a distal portion of the distal core member; and
   b) an inflatable dilatation balloon secured to a distal portion of the elongated torquable member having a distal end sealingly secured about a portion of the distal core element which extends out the distal end of the balloon and having an interior in fluid communication with the inner lumen extending through the proximal tubular element.

2. The steerable dilatation catheter of claim 1 wherein the proximal tubular element has at least one inflation port in a distal portion thereof.

3. The steerable dilatation catheter of claim 2 wherein the balloon has a distal end which is secured to the proximal tubular element at a location proximal to the inflation port.

4. The steerable dilatation catheter of claim 1 wherein the proximal tubular element is formed of nickel-titanium alloy having superelastic properties.

5. The steerable dilatation catheter of claim 1 wherein the distal core element is formed of nickel-titanium alloy having superelastic properties.

6. The steerable dilatation catheter of claim 5 wherein the proximal tubular element is formed of stainless steel.

* * * * *